United States Patent
Wear et al.

(10) Patent No.: US 6,246,747 B1
(45) Date of Patent: Jun. 12, 2001

(54) MULTI-ENERGY X-RAY MACHINE WITH REDUCED TUBE LOADING

(75) Inventors: James A. Wear, Madison; Daniel R. Lenz, Stoughton; Randall K. Payne; Robert A. Washenko, both of Madison, all of WI (US)

(73) Assignee: GE Lunar Corporation, Madison, WI (US)

( * ) Notice: Subject to any disclaimer, the term of this patent is extended or adjusted under 35 U.S.C. 154(b) by 0 days.

(21) Appl. No.: 09/685,267

(22) Filed: Oct. 10, 2000

Related U.S. Application Data
(60) Provisional application No. 60/162,820, filed on Nov. 1, 1999.

(51) Int. Cl.$^7$ .................................................. H05G 1/64
(52) U.S. Cl. ..................................... 378/98.9; 378/98.11
(58) Field of Search ................................. 378/5, 19, 62, 378/98.9, 98.11

(56) References Cited

U.S. PATENT DOCUMENTS

| | | | |
|---|---|---|---|
| 4,792,900 | * 12/1988 | Sones et al. | 600/407 |
| 5,155,365 | * 10/1992 | Cann et al. | 250/363.02 |
| 5,943,388 | * 8/1999 | Tümer | 378/98.9 |

* cited by examiner

Primary Examiner—Robert H. Kim
Assistant Examiner—Allen C. Ho
(74) Attorney, Agent, or Firm—Quarles & Brady LLP

(57) ABSTRACT

An energy discriminator, for distinguishing between high and low x-ray energies in a energy sensitive x-ray machine divides high energies into asymmetric regions. The flux rates in each of the asymmetric regions being used to locate the high-energy region in the appropriate high-energy location even in regions of spectral monotonicity. Because two clearly defined spectral peaks need not be present for accurate location of spectral regions in the output of the detector, less filtering and lower tube loading is required.

19 Claims, 2 Drawing Sheets

MULTI-ENERGY X-RAY MACHINE WITH REDUCED TUBE LOADING

CROSS-REFERENCE TO RELATED APPLICATIONS

This application claims the benefit of U.S. provisional application 60/162,820 filed Nov. 1, 1999 and is incorporated by reference herein.

STATEMENT REGARDING FEDERALLY SPONSORED RESEARCH OR DEVELOPMENT

BACKGROUND OF THE INVENTION

This invention relates generally to multi-energy x-ray machines and in particular to an improved method of discriminating between x-ray energies in such machines that permit lower x-ray flux rates and longer x-ray tube life.

Measuring the x-ray attenuation of an object at two different x-ray energies can reveal the composition of that object as a proportion of two arbitrarily selected basis materials. In the medical area, the basis materials may be "bone" and "soft tissue" allowing x-ray images to yield quantitative information about in vivo bone density for the diagnosis of osteoporosis. Alternatively, the basis "fat" and "lean" tissue may be selected to provide the indication of total body fat useful in the treatment of obesity or conversely wasting diseases.

Basis materials of "explosive" and "nonexplosive" materials may be used in the baggage scanning industry to augment images of the contents of baggage with the indication of the composition of the imaged contents.

Other basis materials may be selected for other industrial applications.

Referring to FIG. 1, a commercially available multi-energy x-ray machine 10, in this case a bone densitometer, includes an x-ray source 12 supported at one end of a C-arm 14 positioned beneath a patient support table 16. An energy sensitive detector 18 is held by the other end of the C-arm 14 opposite the x-ray source receives a fan beam 20 of x-rays from the x-ray source 12. The fan beam is formed by a collimator (not shown) being one or more x-ray opaque shutters which block x-rays in all but narrow rectangular cross section as is well understood in the art.

A patient (not shown) positioned on the patient support table 16 may be scanned by motion of the C-arm with respect to the patient so that the x-ray fan beam 20 illuminates the patient over a region of interest.

Referring now to FIG. 2, the x-ray source 12 may be a conventional polychromatic x-ray tube producing x-rays having a single mode spectrum 22 encompassing both high and low energy x-rays. The x-ray fan beam 20 is received by a k-edge filter 24 such as a cerium filter having an a real density of approximately 343 mg/cm². The effect of the k-edge filter 24 is to preferentially block mid-energy x-rays to produce a bi-modal spectrum 26 having two peaks in regions of high and low energy.

The x-ray fan beam 20 continues through a patient 28 to arrive at an energy sensitive detector 18. Absorption of x-rays by the patient 28 produces at the energy sensitive detector 18 an attenuated bi-modal spectrum 30 also exhibiting the two peaks of bi-modal spectrum 26 but with lower amplitude.

The energy sensitive detector 18 may include a single scanned detector element or a number of detector elements 32 arranged in a linear or a real array. The detector elements in combination with motion of the C-arm (shown in FIG. 1) allow a spatial mapping of x-ray signals to particular lines through the patient 28 and thus imaging of the patient 28 and spatially dependent measurements of the patient 28 such as area densities.

A detector is "energy sensitive" as used herein if it can distinguish the fluence of x-rays at different energies. A number of energy discriminating detector types are known in the art including scintillation-type detectors in which the x-rays are converted to light via a scintillator material. The amount of light for each event indicates the energy of the x-ray photon. The scintillation material may be followed by a photo multiplier tube to amplify the light output and the light may be measured by any of a number of light detectors including but not limited to Charge-Coupled Devices (CCD). Ionization detectors which work by measuring current formed by an ionized gas in the path of the x-rays can provide energy discrimination through measurement of the amount of current generated at each photon event. Solid state detectors using photodiodes can provide energy discrimination through the use of filters in a stacked or side-by-side configuration. Cadmium Zinc Telluride (CZT) provides direct electrical outputs in response to detected x-rays in the form of pulses for each incident photon where pulse amplitude or area is proportional to the photon's energy.

As shown in FIG. 2, the output of the energy sensitive detector 18 for one detector element 32 may be a series of pulses 34 of varying times and heights corresponding to arrival times of related x-ray photons and the energies of those photons. The statistical distribution of the heights of the pulses 34 will conform generally to the attenuated bi-modal spectrum 30.

The signals for each detector element 32 may be received by an amplifier/pulse shaping circuit 35 and then by energy discriminator 36 (only one shown for clarity). The energy discriminator compares each pulse's height to a reference band 38 (implemented by a high and low voltage) which establish a high and low end point of an energy range for a plurality of window comparators 40(a) through 40(c). Generally, only pulses having heights within the corresponding reference band 38 will be passed by the window comparators 40 (i.e., pulse voltage peaks greater than the low voltage and lesser than the high voltage). Window comparators 40 can be constructed by two standard comparators, the first connected to the low references voltage and the pulse signal to provide a low output unless the pulse is above the low reference voltage and the second connected to the high references voltage and the pulse signal to provide a low output unless the pulse is below the high reference voltage. The outputs of the comparators are then logically ANDed together.

Referring now to FIGS. 2 and 4, each reference band 38(a)–(c) generally establishes a different detection zone in the attenuated bi-modal spectrum 30. Reference band 38(c) in conjunction with window comparator 40(c) defines a low energy (LE) range causing the detection of only x-ray photons in the lower peak of attenuated bi-modal spectrum 30. Similarly, ranges 38(a) and 38(b) together, establish with their window comparators 40(a) and 40(b), a high-energy (HE) range detecting photons in the higher energy peak of attenuated bi-modal spectrum 30. Within the HE range, reference band 38(b) further establishes a lower range (LR) and reference band 38(a) establishes an upper range (UR) equally dividing the HE range. The purpose of these sub-ranges will be described below.

Each window comparator 40(a) through 40(c) is followed by an integrator 42 such as a counter which counts the total number of pulses passed by the comparator within the respective ranges LE and HE and subranges LR and UR of range HE.

The output of the integrators 42 is provided to a basis material processor 46 acting on high and low energy attenuation information to establish the composition of the intervening material of the patient 28. The low energy attenuation information is provided directly by the output of the integrator associated with window comparator 40c of the LE range whereas the LR and UR images are added together to form the high energy attenuation information of the HE range. The latter addition is shown by summing block 44.

The basis material processor 46 operates according to well known techniques to process the high and low energy attenuation information to determine a basis material decomposition such as may be displayed to an operator on an interface terminal 48 of conventional design. The basis material processor 46 may be a microprocessor-based computer of a type well known in the art.

Referring now to FIG. 4, variations in the signal chain between the detector elements 32 and the integrators 42 can cause the attenuated bi-modal spectrum 30 to vary in time by a compression or dilation along the horizontal or energy axis as indicated by attenuated bi-modal spectrum 30'. For accurate and repeatable measurements, it is therefore necessary to adjust the HE region to conform with changing location of the high-energy peak of the attenuated bi-modal spectrum 30'. This process of adjusting the location of the HE region provides an automatic gain control and is implemented through use of the lower region LR and upper region UR described above.

Referring now to FIG. 5, the automatic gain control function is implemented continuously or at periodic intervals during the acquisition of data from the energy sensitive detector 18. As indicated by process block 50 in a first step of this process, the received flux in the LR and UR regions are measured being generally the area under the attenuated bi-modal spectrum 30 or 30' within the ranges 38(b) and 38(a), respectively. If the LR flux is greater than the UR flux (plus a deadband E value representing an acceptable error tolerance) such as would be the case, for example, with the attenuated bi-modal spectrum 30 shown in FIG. 4, then this is detected at decision block 52 and at process block 54 the HE region (and LR and UR regions) are moved downward in energy by a predetermined increment.

Contrary-wise, if at decision block 55 it is detected that the LR flux is less than the UR flux (minus a deadband P, value), then the HE region is moved upward in energy (together with the LR and UR regions) per process block 57.

In this way, the HE region is centered on the high-energy peak of the attenuated bi-modal spectrum 30 regardless of the gain of the amplifier and pulse shaping circuitry 35.

In an alternative embodiment, producing the equivalent result, the gain of the amplifier/pulse shaping circuit 35 may be adjusted (along the dotted line path between the range adjuster 56 and the amplifier pulse shaping circuit 35) effectively stretching or shortening the attenuated bi-modal spectrum 30 on the horizontal axis and thus shifting the peak 62 with respect to the LR and UR regions.

Referring to FIG. 2, the process of changing the location of the HE region is performed by a range adjuster 56 which receives the UR and LR value and establishes the ranges 38(a) through 38(c) according to the flow chart of FIG. 5. The range adjuster may be discrete circuitry or may be a program operating on a separate microprocessor or the same microprocessor used for the basis material processor 46.

Referring now to FIG. 6, the comparison of the flux LR and UR regions and process of FIG. 5 serve to position the HE region about a local maximum of the high energy peak of the attenuated bi-modal spectrum 30 or 30'.

Referring again to FIG. 2, the x-ray tube serving as x-ray source 12 will typically be operated at high currents resulting in elevated x-ray tube operating temperatures and a reduced x-ray tube life. This need for high current operation or high tube "loading" results from a number of factors including the low absolute efficiency of x-ray tubes, the high degree of collimation of the x-rays into an x-ray fan beam 20 comporting with the area of the energy sensitive detector 18, the absorption of flux by the k-edge filter 24 and the need for a certain amount of flux for statistical accuracy the measurements being made.

It would be desirable to produce a multi-energy x-ray machine providing improved tube loading that would permit longer tube life.

BRIEF SUMMARY OF THE INVENTION

The present inventors have recognized that a more sophisticated method of distinguishing between the high and low energy regions of the received x-rays can permit the above described automatic gain control to work with an x-ray spectrum in which two peaks are no longer discernable. This in turn permits the k-edge filter (necessary to produce the spectrum peaks) to be substantially "thinned" to absorb less x-rays and thereby to reduce the necessary tube loading. In particular, the present invention provides a gain control circuit that can lock to "monotonic spectral characteristics", that is portions of the x-ray spectrum without peaks.

Specifically, the present invention provides the multi-energy x-ray machine having an x-ray source positioned to produce a beam of x-rays and an energy sensitive x-ray detector positioned to receive the beam of x-rays and produce an output spectra signal indicating x-ray flux according to energy of the received x-rays. An energy discriminator receives the output spectrum and determines x-ray flux in a high and lower energy band of the output spectrum signal. A range adjuster adjusts the relative location of the high and low energy bands based on a monotonic spectral characteristic in the output spectra signal when spectrum maximums in high and low energy bands cannot be distinguished in the output spectrum.

Thus it is one object of the invention to provide automatic gain control that may be used with received x-rays whose spectrum no longer exhibits two distinct peaks.

The loss of spectral peaks may be caused by a thinning of the k-edge filter.

Thus it is a corresponding object of the invention to provide automatic gain control in a multi-energy x-ray machine with a substantially thinner k-edge filter.

The loss of spectral peaks may also be caused by "pile-up" in which the flux rate is too great to be correctly detected by the amplifier/pulse shaping circuitry.

Thus it is a corresponding object of the invention to provide automatic gain control that operates successfully over a wider range of flux rates.

The monotonic spectral characteristic may be a point between average slopes of the output spectrum having a predetermined relationship.

Thus it is another object of the invention to provide a simple method of identifying a unique point on a spectrum or portion of a spectrum that is monotonic. Relative average slopes may be easily deduced in adjacent regions of energy through simple integration of flux over that region.

The energy discriminator may work by determining flux in an upper and lower region of the high-energy band, the lower region being narrower than the upper region. The range adjuster may receive the determination of flux in the lower and upper regions and adjust the relative location of the high- and low-energy band by equalizing the flux in the upper and lower region of the energy band.

Thus it is another object of the invention to provide an extremely simple method of detecting a unique spectral location in monotonic regions of the spectrum, and a method that may work at the high speeds necessary for real-time processing of x-ray events. A simple adjustment of the width of the upper and lower regions used in the prior art devices provides this capability.

The multi-energy x-ray machine may include a k-edge filter positioned between the x-ray source and the x-ray detector for suppressing flux of the x-ray beam between the high and lower energy bans.

Thus it is another object of the invention to permit a thinning of a k-edge filter when a k-edge filter is used so as to reduce tube loading.

The x-ray machine may include a collimator positioned between the x-ray source and the x-ray detector collimating the x-ray beam into a fan beam.

Thus it is another object of the invention to provide decreased tube loading and highly collimated x-ray machines where much of the output x-rays are blocked by collimation blades.

The foregoing and other objects and advantages of the invention will appear from the following description. In the description, reference is made to the accompanying drawings which form a part hereof and in which there is shown by way of illustration a preferred embodiment of the invention. Such embodiment does not necessary represent the full scope of the invention, however, and reference must be made to the claims herein for interpreting the scope of the invention.

DETAILED DESCRIPTION OF THE INVENTION

Figure 1:
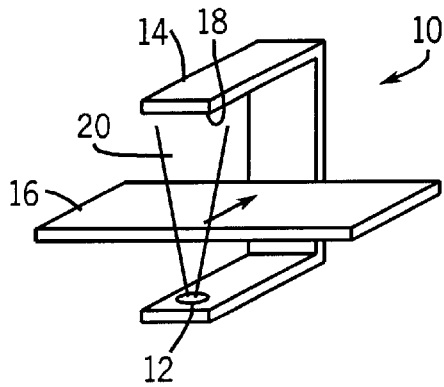
FIG. 1 is a simplified perspective view of a commercially available densitometer for medical use an having opposed x-ray source and x-ray detector scannable across a patient as was described above with respect to the prior art.
Figure 3:
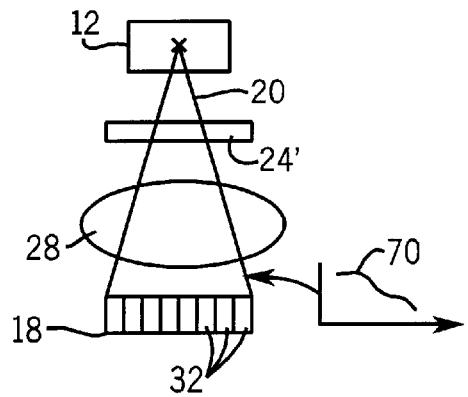
FIG. 3 is a view similar to a portion of FIG. 2 showing a spectrum produced with a reduced thickness k-edge filter or in conditions of high count rates and pile-up not exhibiting distinguishable dual peaks yet accommodated by the present invention.

Referring now to FIG. 3 in the present invention, a decreased tube loading of x-ray source 12 may be accomplished by reducing the density of the k-edge filter 24 as indicated by thinner k-edge filter 24' of FIG. 3. Unfortunately, such a reduction in the k-edge filter thickness can produce a single mode spectrum 70 in which the high and low energy peaks are no longer apparent.

Figure 2:
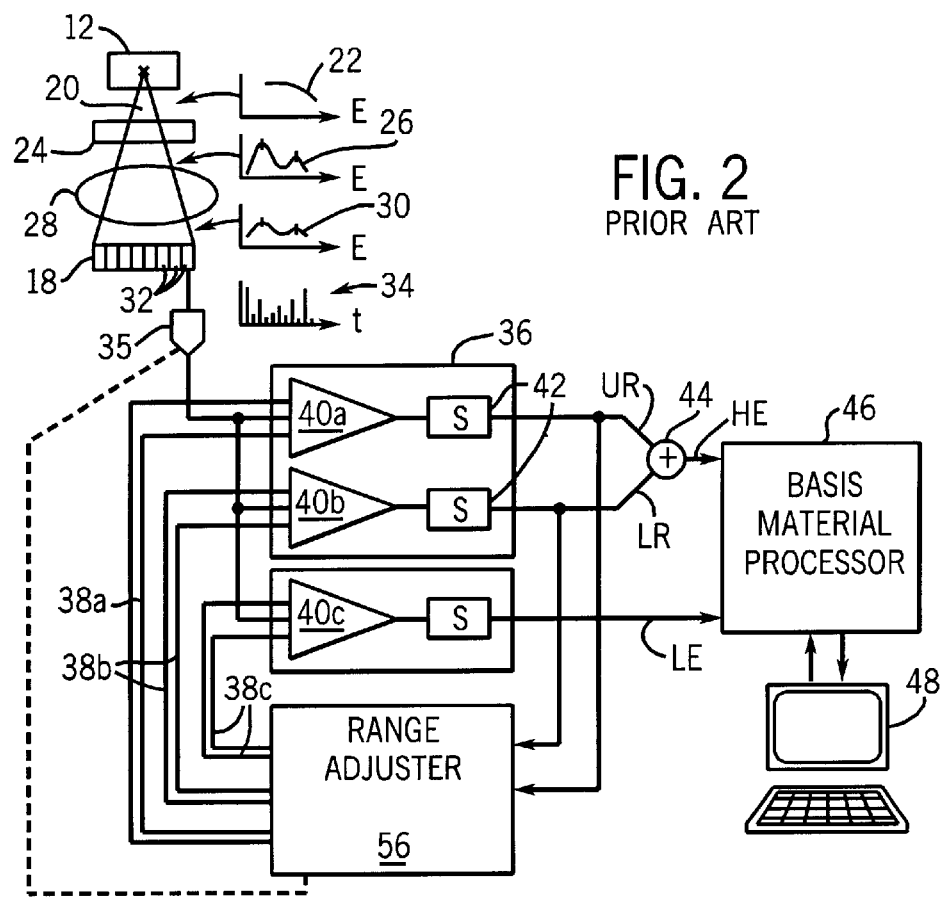
FIG. 2 is a block diagram of the prior art x-ray densitometer of FIG. 1 showing spectra produced at various stages in the x-ray beam as it passes through a k-edge filter and patient to a detector and showing a mechanism for energy range adjustment to lock an energy discriminator onto peaks in the spectrum of received x-rays.
Figure 4:
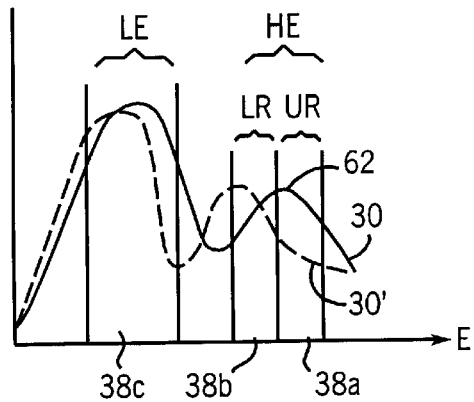
FIG. 4 is an enlarged graph of the spectrum received by the detector of FIG. 2 showing multiple regions established by a prior art energy discriminator as will be adjusted by the range adjuster 56.

The single mode spectrum 70 can result both from the decrease in k-edge filtering and because of the increased flux rates that will now occur at thinner areas of the patient. These increased flux rates produce a condition known as "pile up" in which multiple photon events occur in such close proximity that they cannot be resolved by the amplifier and pulse shaping circuitry 35. When two pulses 34 (shown in FIG. 2) overlap in pile up the result is both lost counts and misinterpreted pulse heights. The error in pulse heights occurs because the pulses have a negative-going portion which may align with a positive going portion of an adjacent pulse resulting in full or partial cancellation of the adjacent pulse.

Figure 7:
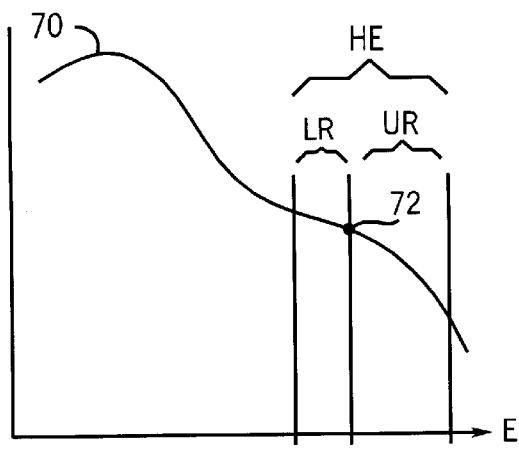
FIG. 7 is an enlarged view of the spectrum of FIG. 3 in which two peaks may not be clearly distinguished and showing an asymmetric division of a high energy range such as allows locking of the energy discrimination circuitry of FIG. 2 onto a monotonic spectral characteristic per the present invention.

Referring now to FIG. 7, a single mode spectrum 70 in the region of the high energy photons is monotonic meaning that it is steadily decreasing (or increasing) without discernible peaks providing transitions between areas of positive and negative slope. For the monotonically decreasing portion of signal mode spectrum 70, the equal size regions LR and UR of the prior art will produce a condition where the LR flux is always greater than the UR flux. For this reason, the prior art range adjuster 56 cannot accommodate a single mode spectrum 70 and will "rollover", a situation where the HE range is continually adjusted downward toward the LE range until it is reset as out of range, resulting in a constant state of adjustment and erroneous values.

The present inventors have recognized that although such single mode spectra 70 do not provide a discernable high energy peak, it is in fact only required that the HE region be locked onto a consistent portion of the single mode spectrum 70 that can be reliably located as the spectrum dilates or contracts with changes in a signal chain gain. A consistent portion of the single mode spectrum 70 is thus identified not as a peak but as an identifiable characteristic of the monotonic portion of the spectrum such as an inflection point or a predetermined slope or relationship of slopes.

Figure 5:
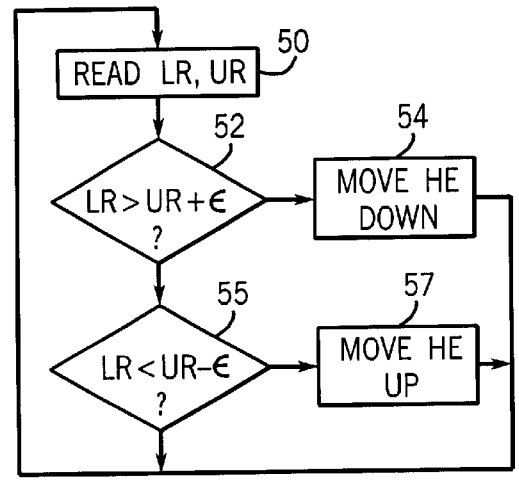
FIG. 5 is a flow chart showing the operation of the range adjuster of the prior art and the present invention in response to measurements of the region of FIG. 4.
Figure 6:
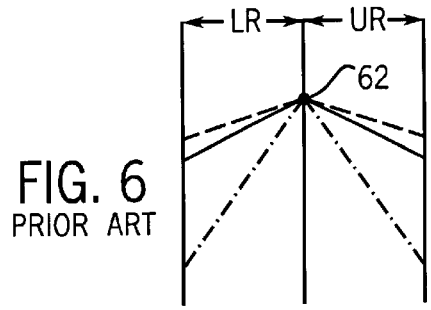
FIG. 6 is a simplified view of a portion of the spectrum of FIG. 4 showing average slopes and the operation of the prior art invention to identify peaks within the spectrum.

The inventors have further determined that at least one monotonic spectral characteristic, that of a point separating average slopes having a predetermined relationship, can be detected by a simple modification of the prior art range adjuster 56 such as breaks the symmetry of the LR and UR regions making the LR region narrower in terms of its span of x-ray energies than the UR region as shown in FIG. 7. With the LR and UR regions properly readjusted, the logic of FIG. 5 is preserved and the range adjuster 56 of the present invention in all other ways operates identically to the prior art range adjuster 56.

Figure 8:
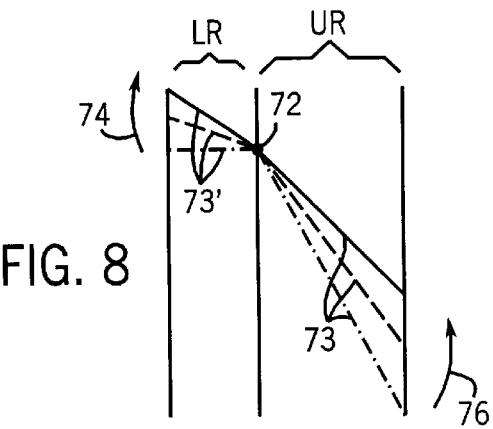
FIG. 8 is a figure similar to that of FIG. 6 showing average slopes discernible by the present invention using the asymmetric regions of FIG. 7.

Referring now to FIG. 8, the range adjuster 56 of the present invention fixes the location of the HE range at a monotonic spectral characteristic point 72 dividing the LR and UR regions so that the areas under the single mode spectrum 70 in these two regions are equal. Such an equality can only be established by a family of different average slopes 73 and 73' that are not equal in magnitude and opposite in sign as in the prior art, but that are of the same sign and have magnitudes that conform to a well defined inequality. Generally as the slope 73' in the LR region is lesser in magnitude than the slope in the UR region and as its magnitude increases as indicated by arrow 74, the magnitude of the slope in the UR region must decrease as indicated by arrow 76.

At extremes of high negative slopes in region UR and high positive slopes in region LR, the algorithm produced by the unequal LR and UR regions devolves to one which will find peaks. However, the point 72 will not be at the crest of the peak and in cases where peaks are not present, a point 72 may still be found.

In this way, the present invention may operate both on single mode spectrum 70 and attenuated bi-modal spectrum 30 transitioning seamlessly between the two spectrum types without rollover. The present invention allows thinning of the k-edge filter and thus a lowering of x-ray tube current and longer tube life. The present invention also permits operation of the multi-energy x-ray machine over a wider dynamic range of fluxes while eliminating lock problems in the automatic gain control caused by pile-up of x-ray events.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

We claim:

1. An energy sensitive x-ray machine comprising:
   an x-ray source producing a beam of x-rays;
   an energy sensitive x-ray detector positioned to receive the beam of x-rays and producing an output spectrum signal indicating x-ray flux according to energy of the received x-rays;
   an energy discriminator receiving the output spectrum and determining x-ray flux into at least a high and low energy band of the output spectrum signal; and
   a range adjuster adjusting the relative location of the high and low energy bands based on a monotonic spectral characteristic in the output spectrum signal when spectrum maximums in high and low energy bands cannot be distinguished in the output spectrum signal.

2. The energy sensitive x-ray machine of claim 1 wherein the monotonic spectral characteristic is a location between average slopes of the output spectrum having a predetermined slope relationship.

3. The energy sensitive x-ray machine of claim 1 wherein the energy discriminator further determines flux in an upper and lower region of the high energy band, the lower region being narrower than the upper region, and where the range adjuster receives the determination of the flux in the upper and lower region and adjusts the relative location of the high and low energy band when spectrum maximums in high and low energy bands cannot be distinguished in the output spectrum signal by equalizing the flux in the upper and lower regions of the high energy band.

4. The energy sensitive x-ray machine of claim 1 including a k-edge filter positioned between the x-ray source and x-ray detector for suppressing flux of the x-ray beam between the high and low energy bands.

5. The energy sensitive x-ray machine of claim 1 wherein the energy sensitive x-ray detector is selected from the group consisting of: a CZT detector, a scintillator detector, and an ionization detector.

6. The energy sensitive x-ray machine of claim 1 including further a basis material processor receiving the determination of the flux in the high and low energy bands and processing them to determine a material composition of object placed between the x-ray source and energy sensitive detector as a composition of at least two basis materials.

7. The energy sensitive x-ray machine of claim 6 wherein the two basis materials are soft tissue and bone.

8. The energy sensitive x-ray machine of claim 6 wherein the two basis materials are explosive and non-explosive materials.

9. The energy sensitive x-ray machine of claim 1 including further a collimator positioned between the x-ray source and the x-ray detector collimating the x-ray beam into a fan beam.

10. A method of energy sensitive x-ray measurement comprising the steps of:
    (a) producing a beam of x-rays having multiple energies;
    (b) receiving the beam of x-rays at an energy discrimination detector and producing an output spectrum signal indicating x-ray flux according to energy of the received x-rays;
    (c) determining x-ray flux in a high and low energy band of the output spectrum signal; and
    (d) adjusting the relative location of the high and low energy bands based on an monotonic spectral characteristic in the output spectrum signal when spectrum maximums in high and low energy bands cannot be distinguished in the output spectrum signal.

11. The energy sensitive x-ray machine of claim 10 wherein the monotonic spectral characteristic is a point between average slopes of the output spectrum having a predetermined slope relationship.

12. The method of claim 10 including the steps of further determining the flux in an upper and lower region of the high energy band, the lower region being narrower than the upper region, and adjusting the relative location of the high and low energy band when spectrum maximums in high and low energy bands cannot be distinguished in the output spectrum signal by equalizing the flux in the upper and lower regions of the high energy band.

13. The method of claim 10 including the step of positioning a k-edge filter between the x-ray source and x-ray detector for suppressing flux of the x-ray beam between the high and low energy bands.

14. The method of claim 10 wherein the energy sensitive x-ray detector is selected from the group consisting of: a CZT detector, a combination scintillator/photomultiplier tube detector, and an ionization detector.

15. The method of claim 10 including further the step of processing the determination of flux of the high and low energy bands to determine a composition of the object placed between the x-ray source and energy sensitive detector as a composition of at least two basis materials.

16. The method of claim 15 wherein the two basis materials are soft tissue and bone.

17. The method of claim 15 wherein the two basis materials are fat tissue and lean tissue.

18. The method of claim 15 wherein the two basis materials are explosive and non-explosive materials.

19. The method of claim 10 including further a collimator positioned between the x-ray source and the x-ray detector collimating the x-ray beam into a fan beam.

* * * * *

UNITED STATES PATENT AND TRADEMARK OFFICE
CERTIFICATE OF CORRECTION

PATENT NO. : 6,246,747 B1
DATED : June 12, 2001
INVENTOR(S) : James A. Wear et al.

It is certified that error appears in the above-identified patent and that said Letters Patent is hereby corrected as shown below:

Column 1,
Lines 54 and 67, change "a real" to -- areal --;

Column 3,
Line 41, change "E value" to -- $\varepsilon$ value --;
Line 48, change "P, value" to -- $\varepsilon$ value --; and Column 6,
Line 46, change "discemable" to -- discernable --.

Signed and Sealed this

Twenty-sixth Day of March, 2002

Attest:

Attesting Officer

JAMES E. ROGAN
Director of the United States Patent and Trademark Office